United States Patent [19]

Jennings, Jr. et al.

[11] Patent Number: 4,643,199

[45] Date of Patent: Feb. 17, 1987

[54] SAFETY BLOOD SAMPLE APPARATUS

[76] Inventors: Baldwin P. Jennings, Jr., 330 Sharon La.; Pamela M. Kivlighan, 314 Berkeley Pl., both of Staunton, Va. 24401

[21] Appl. No.: 834,573

[22] Filed: Feb. 28, 1986

[51] Int. Cl.$^4$ ............................................. A61M 5/32
[52] U.S. Cl. ................................... 128/763; 604/110; 604/198; 604/263
[58] Field of Search ................. 128/760, 763, 765; 604/110, 198, 263

[56] References Cited

U.S. PATENT DOCUMENTS

| | | | |
|---|---|---|---|
| 4,026,287 | 5/1977 | Haller | 604/195 |
| 4,425,120 | 1/1984 | Sampson et al. | 604/198 |
| 4,553,962 | 11/1985 | Brunet | 604/198 |

Primary Examiner—Kyle L. Howell
Assistant Examiner—Randy Citrin
Attorney, Agent, or Firm—B. P. Fishburne, Jr.

[57] ABSTRACT

A sterile barrel and piston assembly with attached aspirating needle is delivered ready for use. Following removal of a needle shield and a reversible safety cap from the rear of the piston, the needle is inserted in a vein and evacuated blood sample tube is inserted in the piston to be penetrated by the rear end of the needle. Following removal of the needle from the vein and removal of the evacuated tube now containing a blood sample, the piston is turned in one direction relative to the barrel of the device to release a first lock between the barrel and piston, followed by retraction of the piston and turning of the piston in the same direction to activate a second lock between the barrel and piston. The safety cap is reversed and re-applied to the rear of the piston where it becomes permanently locked in place. The needle is now safely enclosed within the barrel rearwardly of a safety shield and membrane on the front of the barrel. The non-reusable device is now disposed of according to acceptable practice.

9 Claims, 5 Drawing Figures

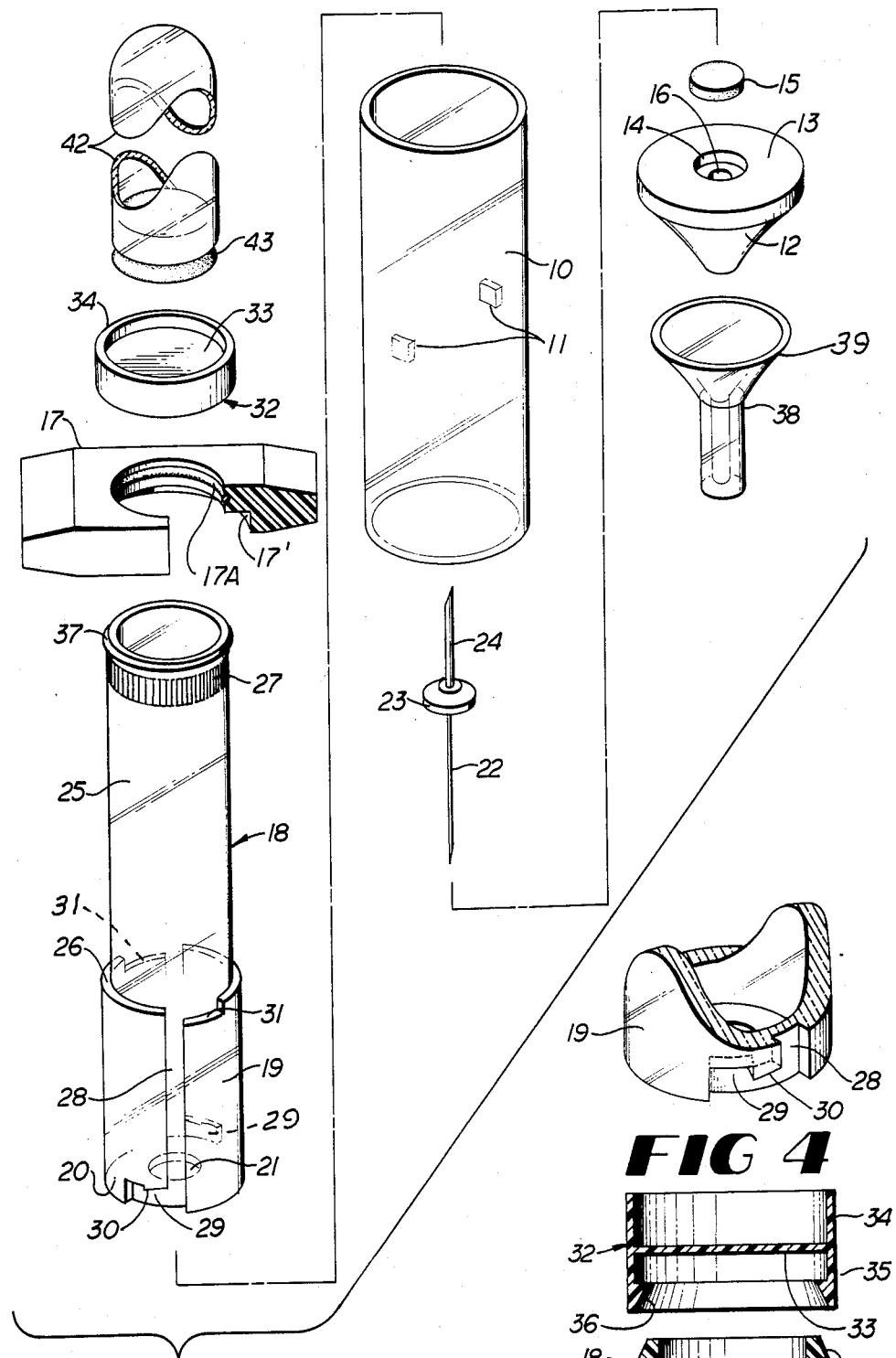

4,643,199

SAFETY BLOOD SAMPLE APPARATUS

Background of the Invention

The present invention relates to an apparatus for taking blood samples from patients for diagnostic testing and the like.

It is customary to utilize sterile single-use disposable devices for this purpose in the same manner that single-use disposable sterile hypodermic needles are widely employed. While these conventional single-use disposable devices fully protect the patient from the dangers of infectious diseases, such as AIDS and certain hepatitis viruses, they include no means to protect medical and hospital personnel from infection due to accidental contact with a contaminated needle or other contaminated part of the disposable apparatus.

Accordingly, it is the prime objective of the present invention to provide a sterile single-use disposable device for taking blood samples from patients, which will not only fully protect the patient but will also fully protect all medical and hospital personnel or others who might come into contact with the device after it is used, and prior to disposal with incineration or the like.

Another important object of the invention is to provide a device of the above-mentioned character which is highly simplified, and therefore relatively economical to manufacture, convenient to use, highly reliable in its operation, and constructed and operated in such a way that spreading infection with the device is almost impossible.

Other objects and advantages of the invention will become apparent to those skilled in the art during the course of the following detailed description.

BRIEF DESCRIPTION OF THE DRAWINGS

FIG. 3 is an exploded perspective view of the invention.

FIG. 4 is an enlarged fragmentary perspective view of a safety locking means.

FIG. 5 is an enlarged fragmentary vertical section taken through a safety locking cap and cooperative elements of a piston.

DETAILED DESCRIPTION

Figures 1, 2:
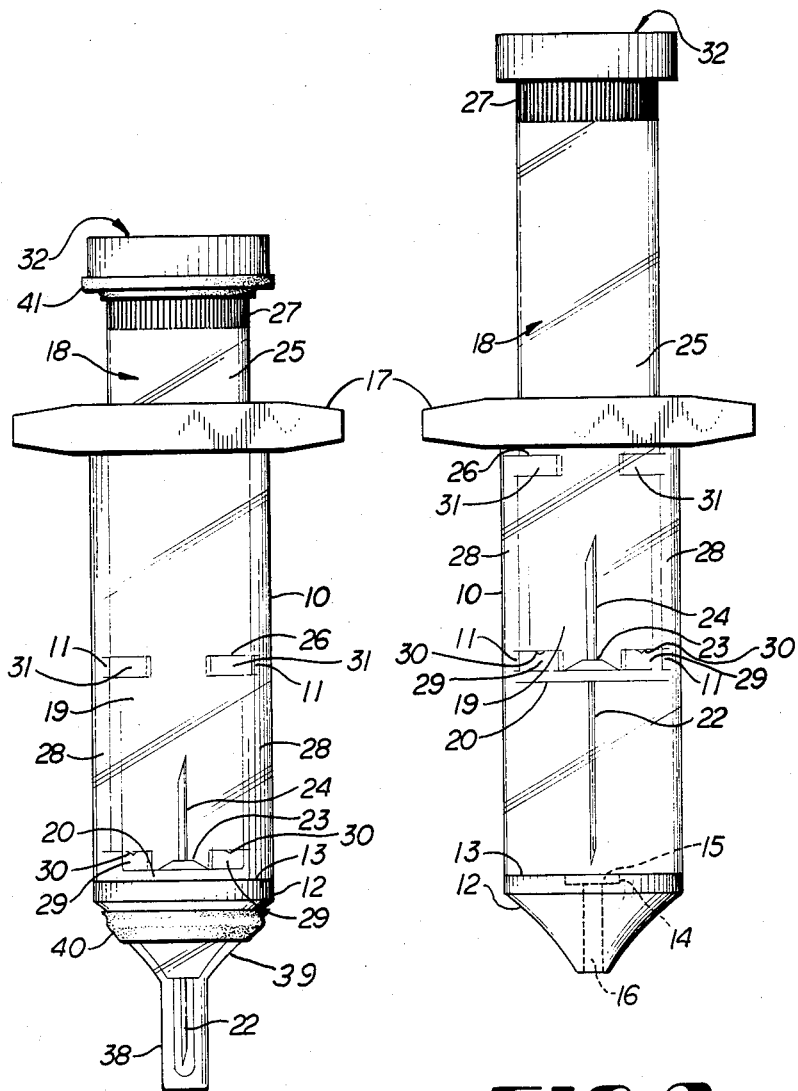
FIG. 1 is a side elevation of a safety blood sample apparatus according to the present invention in a sterile, ready-for-use, condition.
FIG. 2 is a side elevation of the apparatus following use and ready for disposal in a safe locked state.

Referring to the drawings in detail wherein like numerals designate like parts, a safety blood sampling apparatus according to the present invention comprises a barrel 10 provided approximately midway between its two ends with a pair of internal diametrically spaced opposed locking lugs 11 fixed thereto for a purpose to be fully described.

At its forward end, a tapered safety shield 12 is permanently fixed to the barrel 10 and includes an end wall 13 forming a substantial closure for the forward end of the barrel. The safety shield further includes a central aperture 14 formed through the end wall 13 within which a rubber or rubber-like protective membrane 15 is suitably fixedly held. A small diameter central axial bore 16 extends from the aperture 14 and the membrane 15 through the forward end of the safety shield 12. The membrane 15 is located well rearwardly of the forward tip of the safety shield 12. A finger grip element 17 is permanently attached to the rear end of the barrel 10, as shown in the drawings. The element 17 has an opening 17', as shown.

A piston sleeve 18 includes a forward portion 19 having a forward end wall 20 provided with a central opening 21. An aspirating needle 22 includes a hub 23 and a rear somewhat enlarged tubular extension 24. The needle hub 23 is united to the end wall 20 and hermetically sealed with the opening 21, so that the aspirating needle is fixedly and permanently attached centrally to the piston sleeve 18 with its rear extension 24 projecting rearwardly of the end wall 20 and into the portion 19 of the piston sleeve. The portion of the needle 22 forwardly of the hub 23 extends well forwardly of the end wall 20.

The piston sleeve further includes a rear somewhat reduced diameter portion 25 forming a narrow annular shoulder 26 on the piston sleeve where the two portions 19 and 25 are joined. The interior diameter of the piston sleeve 18 can be constant from end-to-end thereof. At its rear end, the sleeve portion 25 is preferably serrated at 27 or otherwise roughened to facilitate rotating the piston sleeve on its longitudinal axis at required times. Preferably, the finger grip element 17 carries an elastic O-ring 17a within a recess thereof which has a wiping action on the periphery of the portion 25 of piston sleeve 18.

The piston sleeve 18 is provided in its forward portion 19 on diametrically opposite sides with a pair of straight longitudinal slots 28 cut into the side wall thereof. At their forward ends, these slots 28 communicate with circumferentially extending slot extensions 29 which extend oppositely on the two diametrically opposite sides of the device. Each circumferential slot extension 29 has a stepped locking surface 30 for cooperative locking engagement with the two barrel lugs 11 at proper times. At their rear ends, the longitudinal slots 28 communicate with oppositely circumferentially extending locking recesses 31, also adapted to receive the two locking lugs 11 at required times, as will be further explained. The elements 29 and 31 of each slot 28 also extend oppositely circumferentially at the end of each slot 28, as shown in the drawings. The recesses 31 are cut into the annular shoulder 26 of the piston sleeve.

The apparatus further comprises a reversible safety closure cap 32 for the rear end of piston sleeve portion 25. The cap 32 has an intermediate flat web 33, one plain annular skirt 34 projecting from one side of the web 33, and another skirt 35 extending from the opposite side of the web 33 and carrying reversely extending spring locking elements 36 or a single somewhat yielding locking element. The cap 32 is reversible in its application to the rear end of piston sleeve portion 25. The latter is equipped with a rear end externally enlarged locking bead 37 for cooperative snap locking engagement with the cap yielding element 36 or plural elements.

The apparatus further includes a removable needle shield 38 with which the device is equipped at the time of delivery for use in a sterile state, FIG. 1. The flared end 39 of the needle shield 38 engages over the tapered safety shield 12 and is temporarily secured by frangible tape 40. Similarly, frangible tape 41 is employed to temporarily secure the reversible cap 32 to the rear of the piston sleeve 18 in the non-locking position where the plain annular skirt 34 has a simple slip fit over the bead 37.

Finally, the apparatus makes use of a standard commercial pre-evacuated blood receptor vial 42 having a needle-puncturable rubber stopper 43 in one end thereof.

The operation of the safety blood sample apparatus is as follows.

The apparatus in its assembled state, and in a completely sterile condition, is received by a user in the condition shown in FIG. 1. The reversible cap 32 in the non-locking position is taped onto the rear end of the piston sleeve 18, and the needle shield 38 is taped onto the safety shield 12 to enclose and protect the needle 22 as described.

The piston sleeve 18 is in its forwardmost position and the rearward locking recesses 31 of the piston sleeve have the locking lugs 11 of the barrel 10 engaged therein, so that the piston sleeve is now locked in the forward position shown in FIG. 1. The assembly is sterile and ready for use for drawing blood, as previously explained.

The needle shield 38 and the closure cap 32 are now twisted and removed, the tapes 40 and 41 breaking away in response to the twisting action.

The needle 22 is now thrust into a patient's vein and the evacuated tube or vial 42 is inserted into the open rear end of the piston sleeve 18 until the rear needle extension 24 penetrates the stopper or membrane 43. When this occurs, blood will immediately enter the vial 42 due to the partial vacuum therein. No other action by the user is required to cause the transfer of blood to the vial 42.

The vial 42 is now removed from the rear end of piston sleeve 18. The user now grips the barrel 10 or finger grip 17 while twisting the piston sleeve 18 counterclockwise to disengage the lugs 11 from the recesses 31. Following this, the piston sleeve 18 is pulled rearwardly from the barrel 10 toward the position shown in FIG. 2, during which movement the locking lugs 11 which remain stationary pass through the longitudinal slots 28 leading to the circumferential slot extensions 29 having the stepped locking surfaces 30, FIG. 4. The piston sleeve 18 is now turned counterclockwise until the lugs 11 engage the stepped locking surfaces 30 with a snap action, whereupon the piston sleeve is securely and permanently locked against movement in any direction, rotationally or longitudinally, relative to the barrel 10.

It is to be noted that the contaminated needle 22 is now fully withdrawn into the interior of the barrel 10 and rearwardly of the safety shield 12 and its rubber membrane 15 which the needle was previously penetrating while the device was in the use position of FIG. 1. With the device locked in the safety disposable position of FIG. 2, there is no possibility of anyone touching the needle 22, the interior of the barrel 10 or even the membrane 15.

The reversible safety cap 32 is now placed on the rear of the piston sleeve 18 in the locking position, wherein the locking flange or flanges 36 are snap locked behind the locking bead 37 of the piston sleeve. The device can now be disposed of in the acceptable manner as by incineration or the like.

It should be noted that the membrane 15 in the position shown in FIG. 2 will retain any secretions safely in the barrel 10. The membrane 15 is protected by the safety shield 12.

The advantages of the device over the prior art will now be readily apparent to those skilled in the art.

It is to be understood that the form of the invention herewith shown and described is to be taken as a preferred example of the same, and that various changes in the shape, size and arrangement of parts may be resorted to, without departing from the spirit of the invention or scope of the subjoined claims.

We claim:

1. A safety blood sample apparatus or the like comprising
   a telescopically interfitting barrel and piston sleeve each having forward and rear ends and being adapted for relative axial and rotational movements,
   interengageable locking means on the barrel and piston sleeve enabling the piston sleeve to be locked relative to the barrel in a forward position and a retracted position,
   a tubular needle on the forward end of the piston sleeve extending forwardly and rearwardly of said forward end and adapted to be bodily enclosed within the barrel and piston sleeve when the piston sleeve is locked in the retracted position, and
   a safety needle shield carried by the forward end of the barrel and having a needle through opening and an elastic membrane extending across an inner end of said through opening, said through opening and membrane being substantially coaxially aligned with said needle, and
   closure cap means for non-releasably lockingly engaging the rear end of the piston sleeve when the piston sleeve is in said second retracted position.

2. A safety blood sample apparatus comprising
   a barrel having a forward end and a rear end having locking means thereon between its ends,
   a needle safety shield including an elastic membrane on the forward end of the barrel,
   a piston sleeve having a forward end and a rear end slidably engaged within the barrel for longitudinal and rotational movement therein and being adapted to receive through its rear end removably an evacuated fluid receptor tube having a forward puncturable elastic closure element,
   an aspirating needle fixed to the forward end of the piston sleeve centrally and having parts extending forwardly and rearwardly of said forward end of the piston sleeve, said needle being coaxially aligned with said safety shield and the elastic membrane thereof,
   first locking means on the piston sleeve between its forward and rear ends for lockingly engaging with the locking means of the barrel to hold the piston sleeve in a first forward position in the barrel with the aspirating needle penetrating the elastic membrane of the needle shield and extending forwardly of the safety shield, and second locking means adjacent the forward end of the piston sleeve for lockingly engaging with the locking means of the barrel in a second rear position following rotation of the piston sleeve from the first forward position in one direction relative to the barrel, longitudinal retraction of the piston sleeve, and rotation of the piston sleeve in the same direction, thereby holding the piston sleeve immovably locked in said second rear position on said barrel with said needle contained wholly within the barrel and piston sleeve rearwardly of the needle safety shield and its elastic membrane, and closure cap means for non-releasably lockingly engaging the rear end of the piston sleeve when the piston sleeve is in said second rear position.

3. A safety blood sample apparatus as defined in claim 2, and the locking means on the barrel comprising a pair of diametrically opposite locking lugs fixed to the inside of the barrel, and the first and second locking means on the piston sleeve each comprising pairs of diametrically opposite circumferential locking recesses formed in the piston sleeve at its forward end and between its ends respectively and extending in opposite circumferential directions, and the piston sleeve having diametrically opposite longitudinal slots formed therethrough in communication with the first and second locking recesses, whereby the locking lugs of said barrel can pass through said slots in order to move into locking engagement with the first and second locking recesses of the piston sleeve.

4. A safety blood sample apparatus as defined in claim 3, and the first locking recesses of the piston sleeve having stepped locking surfaces which prevent relative rotation of the barrel and piston sleeve when the first locking recesses of the piston sleeve are lockingly engaged with said lugs of said barrel.

5. A safety blood sample apparatus as defined in claim 2, and said closure cap comprising a reversible cap having an intermediate wall, an annular skirt projecting beyond one side of the intermediate wall, and a locking skirt projecting beyond the other side of said wall, and the rear end of the piston sleeve having a locking bead thereon, wherein the reversible closure cap can be applied removably to the rear end of the piston sleeve through said annular skirt and can be non-releasably locked to the rear end of the piston sleeve through said locking skirt and said bead.

6. A safety blood sample apparatus as defined in claim 2, and a finger grip element secured to the rear end of the barrel and having an opening movably receiving the piston sleeve therethrough, and an elastic ring element on the finger grip element having wiping engagement with the piston sleeve.

7. A safety blood sample apparatus as defined in claim 6, and the piston sleeve comprising a rearward portion and a somewhat diametrically enlarged forward portion, and said first and second locking means on the piston sleeve being disposed on said enlarged forward portion.

8. A safety blood sample apparatus as defined in claim 2, and the piston sleeve including a forward end wall having a central aperture, and said needle being fixedly anchored to said forward end wall through said aperture.

9. A safety blood sample apparatus as defined in claim 2, and a protective removable needle shield enclosing the part of the aspirating needle which projects forwardly of the needle safety shield when the piston sleeve is locked to the barrel by the interengagement of the locking means of the barrel with the first locking means of the piston sleeve, and frangible tapes securing the removable needle shield to said needle safety shield and securing the closure cap to the rear end of the piston sleeve.

* * * * *